United States Patent [19]

Green

[11] 4,127,227
[45] Nov. 28, 1978

[54] WIDE FASCIA STAPLE CARTRIDGE

[75] Inventor: David T. Green, Norwalk, Conn.

[73] Assignee: United States Surgical Corporation, Stamford, Conn.

[21] Appl. No.: 730,822

[22] Filed: Oct. 8, 1976

[51] Int. Cl.² .......................... B25C 5/02; B25C 5/16
[52] U.S. Cl. ..................................... 227/83; 227/19; 85/49
[58] Field of Search ............... 227/19, 108, 83; 85/49

[56] References Cited

U.S. PATENT DOCUMENTS

| | | | |
|---|---|---|---|
| 1,910,688 | 5/1933 | Goodstein | 85/49 |
| 2,764,758 | 10/1956 | Schafroth | 227/108 |
| 2,778,266 | 1/1957 | Forrester | 85/49 |
| 2,987,725 | 6/1961 | Heilman | 227/108 |
| 3,077,812 | 2/1963 | Dietrich | 85/49 |
| 3,618,842 | 11/1971 | Bryan | 227/19 |
| 3,638,847 | 2/1972 | Noiles et al. | 227/19 |
| 3,650,453 | 3/1972 | Smith, Jr. | 227/19 |
| 3,717,294 | 2/1973 | Green | 227/19 |
| 4,014,492 | 3/1977 | Rothfuss | 85/49 |

FOREIGN PATENT DOCUMENTS

| | | | |
|---|---|---|---|
| 932,998 | 9/1973 | Canada | 85/49 |
| 823,878 | 11/1959 | United Kingdom | 85/49 |

Primary Examiner—Granville Y. Custer, Jr.
Attorney, Agent, or Firm—Fleit & Jacobson

[57] ABSTRACT

A cartridge is provided for applying staples to the disunited fascia of a patient. The cartridge is adapted to associate with a surgical stapling instrument which supplies rectilinear thrust to power the cartridge. The cartridge houses a plurality of staples mounted on a flexible belt. A pusher is slidably mounted in the cartridge for forming the staples around an anvil. A spring pawl associated with the pusher moves the staples into a position ready to be fired as the forwardmost staple is being formed around the anvil. As a staple is formed around the anvil, a spring associated with the cartridge cover holds the staple against the anvil. This spring also provides the function of ejecting the staple from the cartridge after it has been formed. On the return stroke of the pusher, a spring pawl arrangement associated with the cartridge cover prevents the belt and staples from moving rearward away from the anvil. The staples have a wide spacing between the points of the staple arms and enclose a large amount of fascia as the arms of the staples sweep through an arc as the staples ae being formed. Also, the staples are formed into a configuration in which the arms of the staples resist being pulled apart so that the staples will not be inadvertently disconnected from the fascia.

20 Claims, 18 Drawing Figures

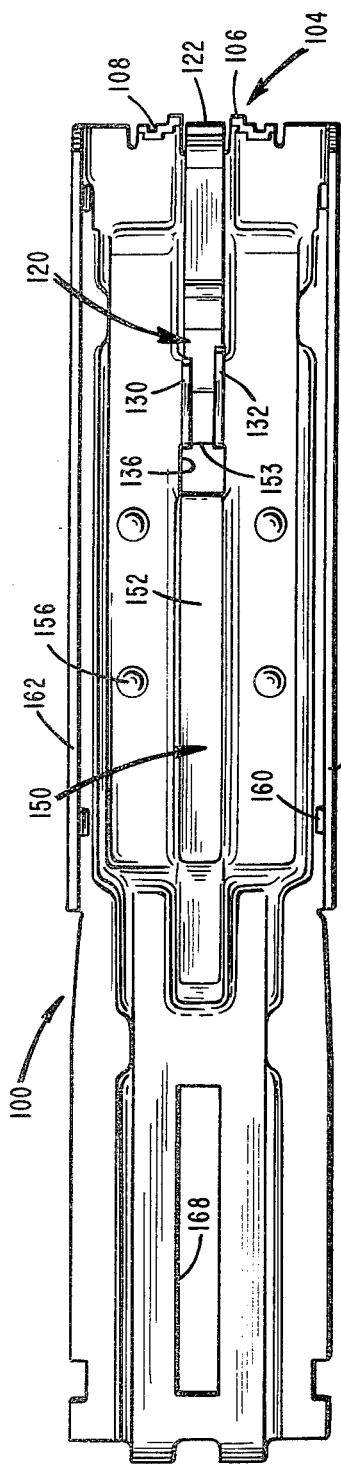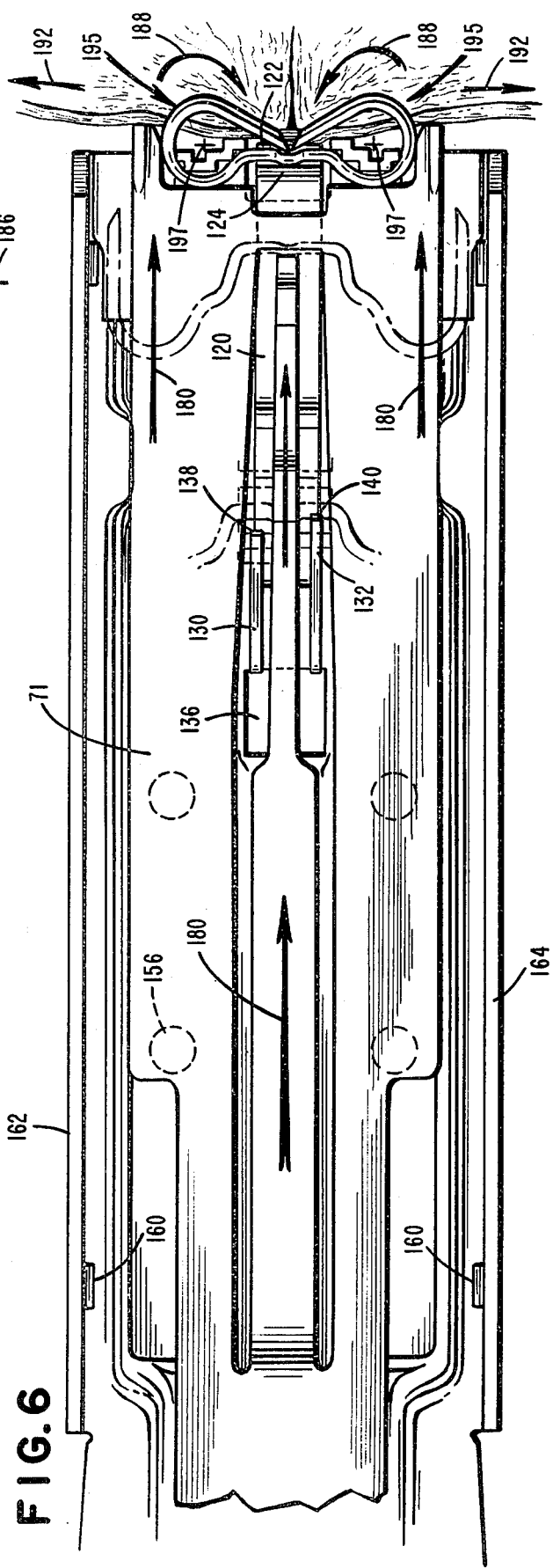
FIG. 4
FIG. 5
FIG. 6

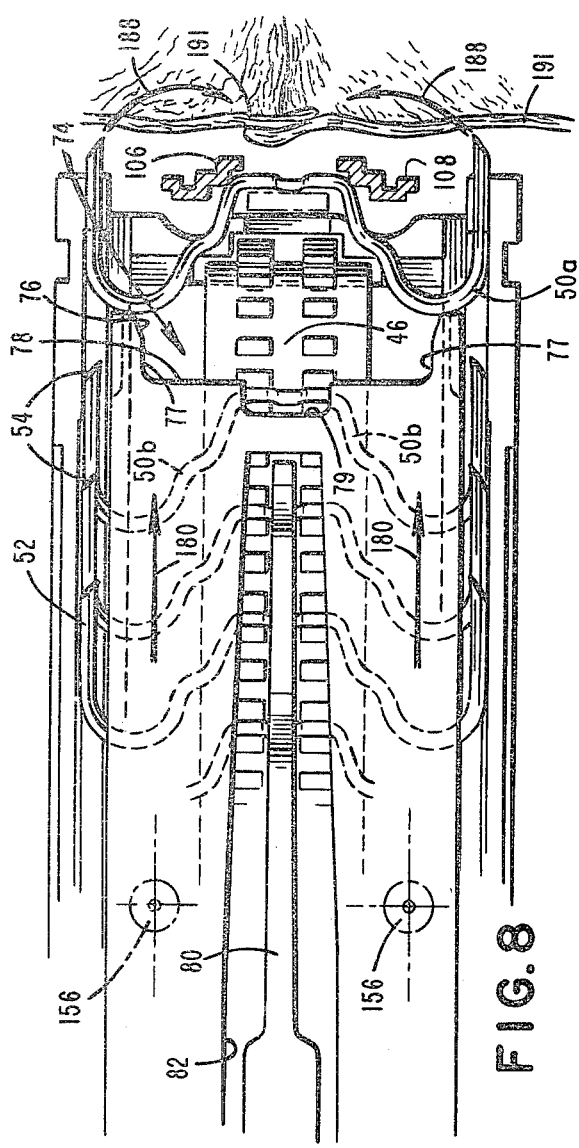
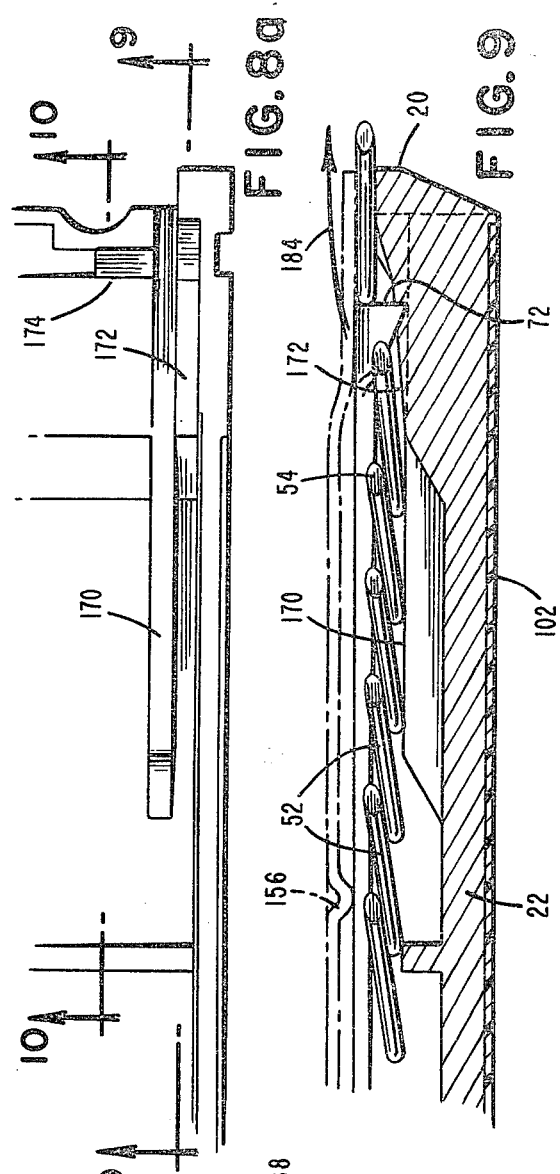
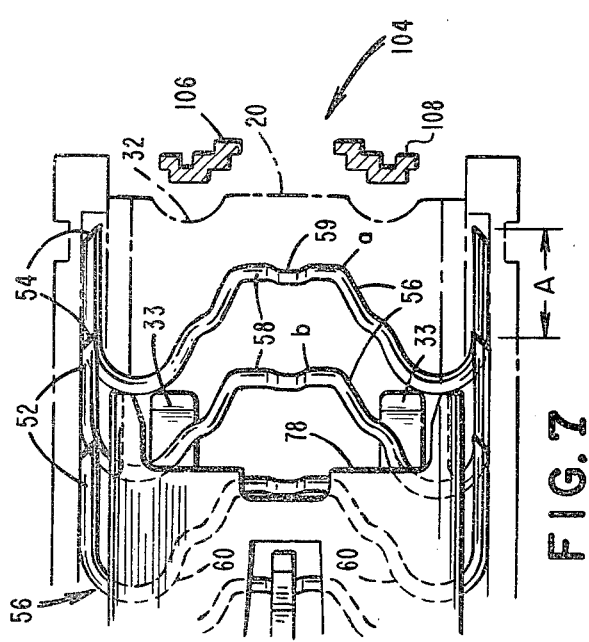
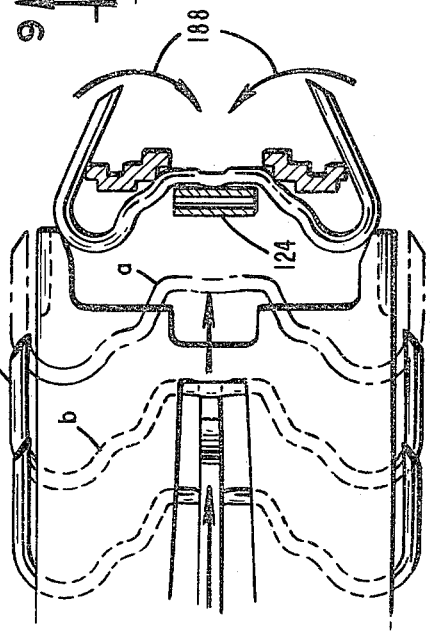

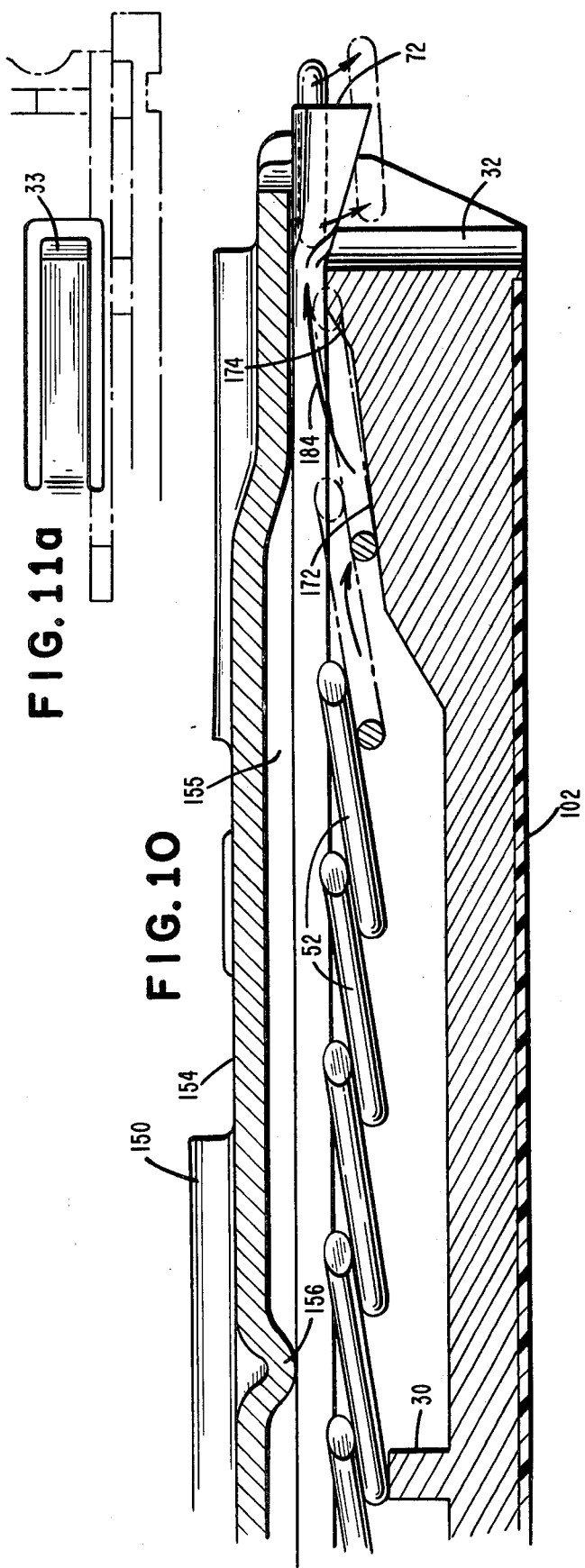
FIG. 11a
FIG. 10
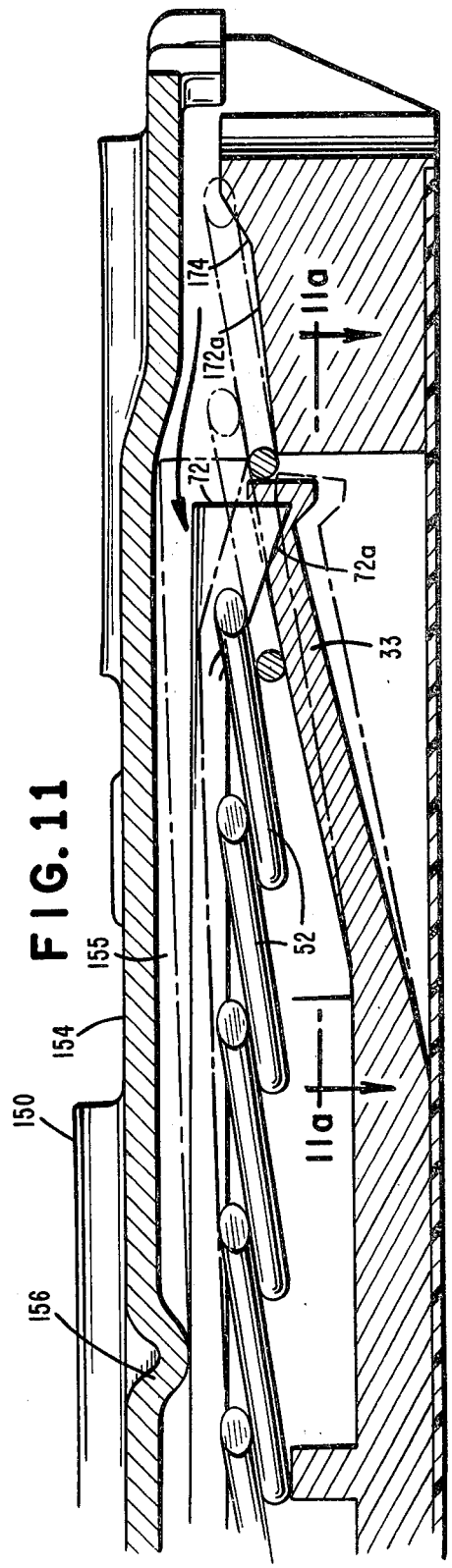
FIG. 11

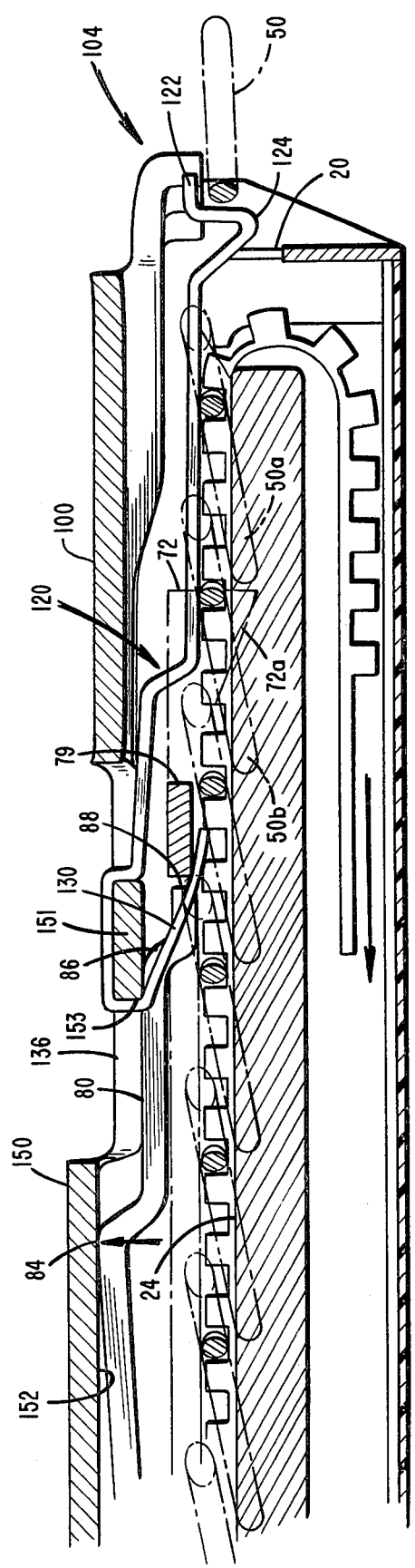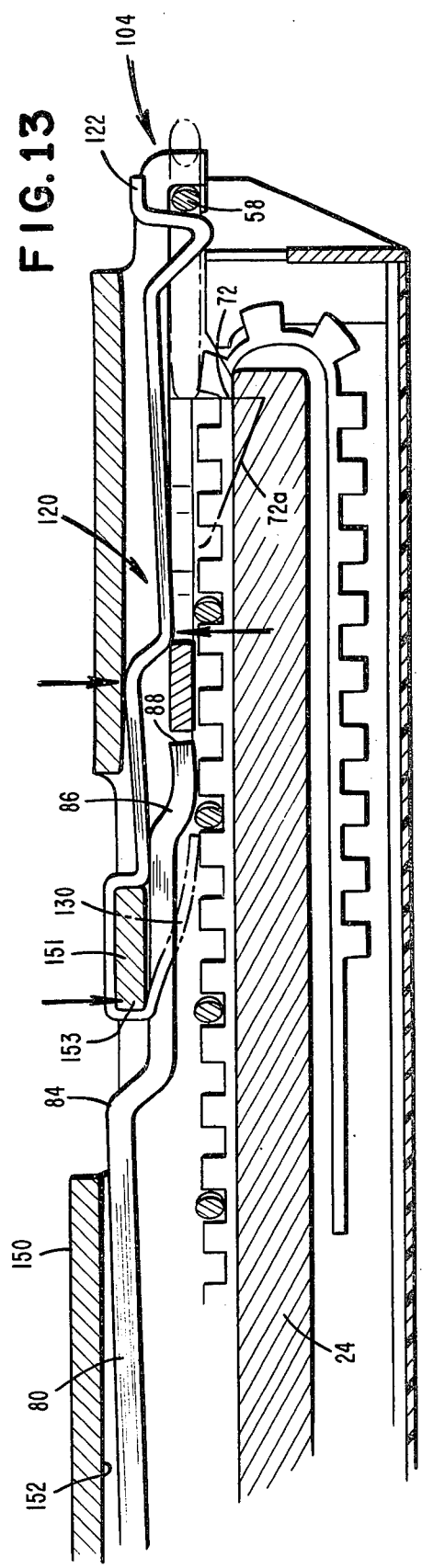

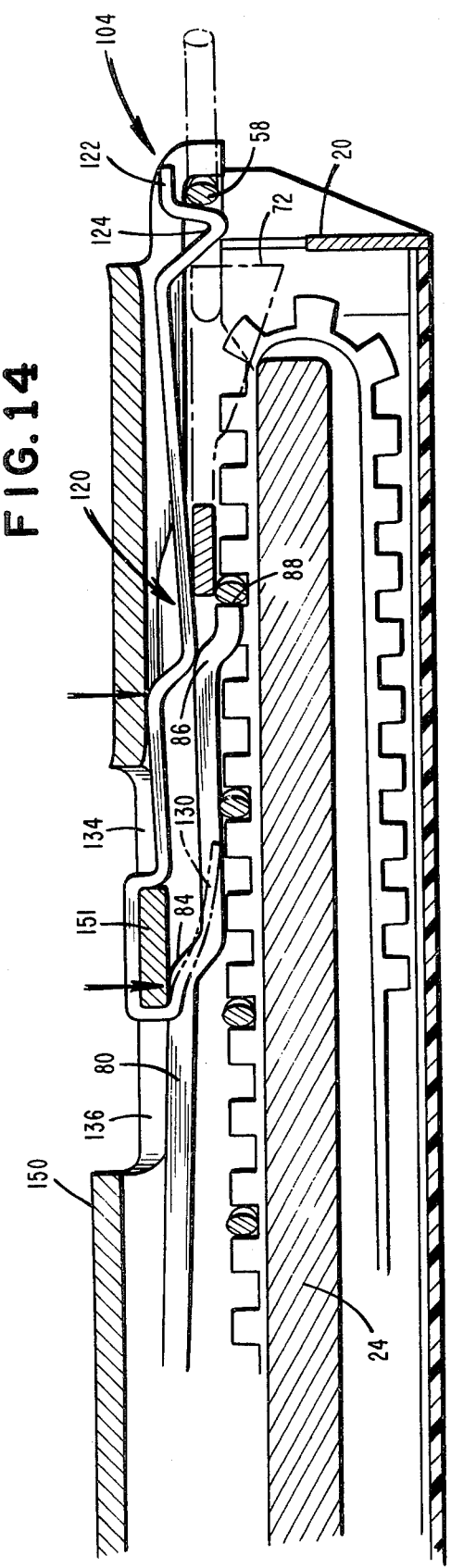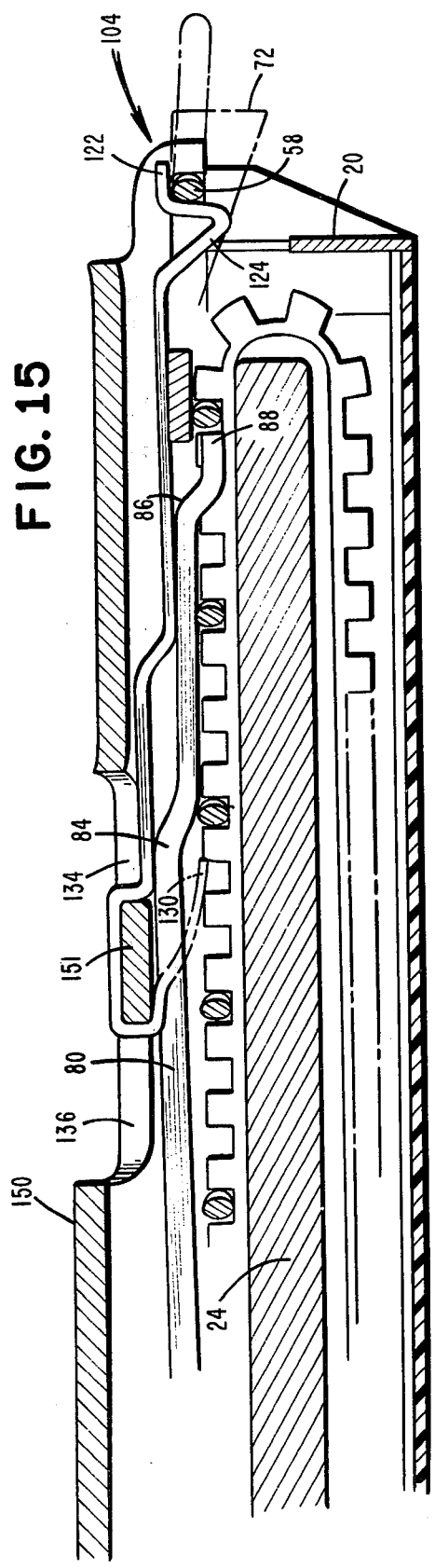

WIDE FASCIA STAPLE CARTRIDGE

BACKGROUND OF THE INVENTION

Recently, staple-carrying cartridges have been designed which eliminate the requirement for the complex gearing once needed in the powering of a surgical stapling instrument. With these cartridges, the output shaft or thrust bar of the powering instrument need only have rectilinear thrust capabilities. The staples are advanced by means designed into the cartridges themselves. In commonly assigned U.S. Pat. No. 3,618,842, the advancing pusher, integral with the cartridge, rotates a pair of staple-driving screws by means of cams formed in the rear portions of the screws. In commonly assigned U.S. Pat. No. 3,638,847, the staples are driven forward by the interaction of pairs of opposing ratchet teeth integral with the cartridge.

More recently, in commonly assigned U.S. Pat. No. 3,650,453, the staple-carrying cartridge includes a flexible belt moveably housed in the cartridge body. Staples are guided and advanced by association with spaced teeth on the flexible belt. The cartridge is equipped with an anvil integral with the cartridge body and a pusher which advances the staples and singly forms the same. Further improvements and modifications to the belt cartridge are disclosed in commonly assigned U.S. Pat. No. 3,717,294.

These prior cartridges are adapted to house staples which have a "U" configuration prior to being formed around the anvil. The pusher and associated anvil are then adapted to form the staples into a rectangular configuration in which the points of the staples abut. Although staples formed in this manner have proved satisfactory in practice, there are certain disadvantages associated with these staples, particularly when joining together disunited fascia. In particular, the points of the staples do not enclose as much fascia during the formation of the staples as desired. Moreover, in the final configuration, with the points of the staples abutting, the staples do not have as much resistance to being pulled apart as desired. For these and other reasons, it would be advantageous to have improved staples and an associated cartridge adapted to accept these staples which avoids the disadvantages mentioned above.

Accordingly, it is a broad object of this invention to provide a new staple design for stapling the disunited fascia or similar living tissue of a patient.

It is another object of this invention to provide a new staple design in which the points of the arms of the staple are widely spaced apart and enclose a large amount of fascia as the arms of the staple sweep through an arc during staple formation.

It is still another object of this invention to provide a new staple design in which the arms of the staple, after formation, resist being pulled apart.

It is yet another object of this invention to provide a staple-carrying cartridge which is adapted to accept the new staples.

Another object of this invention is to provide a staple-carrying cartridge which has improved means for advancing, forming and ejecting the staples.

These and other objects of the invention, as well as many of the attendant advantages thereof, will become more readily apparent when reference is made to the following description taken in conjunction with the accompanying drawings.

SUMMARY OF THE INVENTION

This invention relates to an improved staple and associated cartridge adapted to accept the staple for stapling together disunited segments of fascia of a patient.

The improved staple comprises a configuration, prior to formation, in which the points of the staple arms are widely spaced apart. The staple also has a cross-piece which includes a transverse center section perpendicular to the arms of the staple which is adapted to abut against an anvil. The spaced apart arms of the staple and the transverse center section are connected by two arcuate sections. With this design, the points of the staple enclose a large amount of fascia as the arms sweep through an arc during staple formation. Also, after formation, the points of the staple abut against the transverse center section of the staple to form a staple configuration which resists pulling apart.

The improved cartridge houses a plurality of staples mounted on a flexible belt so that the staple arms overlap in a "shingle" arrangement. A pusher is slidably mounted in the cartridge for moving each forwardmost staple up a series of ramps out of the plane of the belt and forming the staples around an anvil. A spring pawl associated with the pusher moves the second forwardmost staple and the belt into a position where the staple is ready to be fired in the subsequent operation of the cartridge as the forwardmost staple is being formed around the anvil. As a staple is formed around the anvil, a spring associated with the cartridge cover holds the staple against the anvil. This spring also provides the function of ejecting the staple from the cartridge after it has been formed. On the return stroke of the pusher, a pair of spring pawls associated with the cartridge cover prevents the belt and staples from moving rearward away from the anvil. In addition, a pair of spring pawls associated with the cartridge body is provided to prevent backing up of the forwardmost staple during the return stroke of the pusher.

BRIEF DESCRIPTION OF THE DRAWINGS

FIG. 4 is a bottom plan view of the cartridge cover;

FIG. 5 is a side view of the pusher showing its association with the thrust bar of a surgical stapling instrument shown in phantom lines;

FIG. 6 is a bottom plan view of the pusher associated with the cartridge cover and showing the staples in various stages of advance;

FIG. 7 is a top plan view of the cartridge with the cover removed showing the staples in their initial ready position;

FIG. 8 is a top plan view of the cartridge with the cover removed showing the pusher moving the first staple into abutment with the anvil;

FIG. 8a is a top plan view of the cartridge with the cover, pusher and staples removed showing the ramps for moving the staples out of the plane of the belt and into the plane of the main portion of the pusher;

FIG. 9 is a vertical cross-sectional view taken along line 9—9 in FIG. 8a with the pusher and staples illustrated in the same position shown in FIG. 8;

FIG. 10 is a vertical cross-sectional view taken along line 10—10 in FIG. 8a with the pusher and staples illustrated in the same plane as FIG. 9, showing the pusher in its forwardmost position and the staple completely formed;

FIG. 11 is a vertical cross-sectional view showing the spring pawl associated with the cartridge body to prevent backing up of the forwardmost staple during the return stroke of the pusher;

FIG. 11a is a top plan view of a part of the cartridge body showing the spring pawls of FIG. 11 taken along line 11a—11a in FIG. 11;

FIGS. 12-15 are a series of four vertical cross-sectional views showing the mechanism for advancing the second forwardmost staple and the belt, for preventing the belt and staples from moving rearward, for holding the staple against the anvil while the staple is being formed, and for ejecting the staple;

FIG. 16 is a diagrammatical view of the association between the pusher and the staples as the forwardmost staple in the cartridge is being formed around the anvil and the remaining staples are being advanced in the cartridge.

DESCRIPTION OF THE PREFERRED EMBODIMENTS

Figure 1:
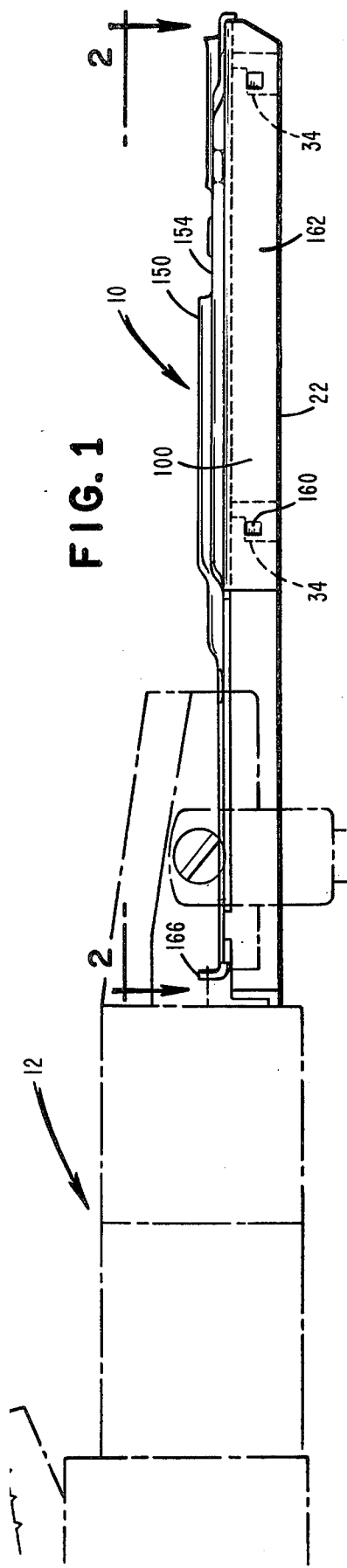
FIG. 1 is a side view of the staple-carrying cartridge showing its association with a surgical stapling instrument shown in phantom lines.

The cartridge is shown generally at 10 and, in FIG. 1, is mounted on a surgical stapling instrument 12. The surgical stapling instrument may be any conventional instrument having rectilinear thrust capabilities. Suitable instruments are shown, for example, in commonly assigned U.S. Pat. No. 3,949,924 and Re No. 28,932.

As shown in FIGS. 1-3, 7, 11, 11a and 12 the cartridge 10 comprises a main body 14, typically made of a rigid plastic material, having a pair of side walls 16 and 18, respectively, a front wall 20 and a bottom wall 22. The center portion of the bottom wall is formed into a longitudinally extending guide base 24 which projects upwardly from the plane of the bottom wall. Belt openings 26 and 28 are formed in main body 14 at the forward and rear longitudinal ends of the guide base 24. A plurality of reinforcing ribs 30 extend transversely between the side walls 16 and 18 and the respective sides of the guide base 24. The front wall 20 has a pair of concave recesses 32 to permit ejection of the staples after formation. In addition, a pair of spring pawls 33 are defined by the main body 14 to prevent backing up of the forwardmost staple during the return stroke of the pusher. The spring pawls 33 are only shown in FIGS. 11 and 11a, and in phantom in FIG. 7, to simplify the drawings. Finally, slots 34 are formed in the outer side walls 16 and 18 for fastening the cartridge cover.

A belt 40, made of a flexible plastic such as "Lexan" or polypropylene, is mounted on the guide base 24 to form a loop which passes through the belt openings 26 and 28 at each end of the guide base. The belt 40 is substantially planar in configuration and has a plurality of longitudinally spaced apart pairs of teeth 42 on one side thereof, between which teeth are defined a plurality of staple-carrying grooves or contact surfaces 44. The plurality of longitudinally spaced apart pairs of teeth 42 define two longitudinally extending rows of teeth between which are defined a longitudinally extending groove 46.

A staple 50 is received in and guided by every third staple carrying groove 44 of the belt 40. As shown in FIG. 7, the staples, as mounted in the belt, have a pair of arms 52 terminating in points 54 which extend in the longitudinal direction of the main body 14 of the cartridge 10. The staples 50 also have cross-pieces 56 which include transverse center sections 58 which extend transversely of the arms 52 and the belt 40. The transverse center sections 58 of the staples 50 are fitted into the staple-carrying grooves 44. The center portions of the transverse center sections 58 are flattened at 59. Connecting the arms 52 and the transverse center sections 58 of the staples 50 are two arcuate sections 60. With this configuration, the points 54 of the staples are widely spaced apart and the transverse center sections 58 are positioned relatively near a line drawn between the points 54. The staples 50 are mounted on the belt 40 so that the points 54 of each of the staples, with the exception of the forwardmost staple, rests upon the arms of the preceding staple in "shingle" fashion.

Referring now to FIG. 5, a substantially planar pusher 70 is positioned above the belt 40 and the staples 50 carried thereon and is adapted for movement longitudinally within the cartridge 10. As best seen in FIG. 9, while the pusher 70 lies above the plane of the top of the transverse center sections 58 of the staples 50, a pair of downwardly projecting flanges 72 at the forward end of the pusher 70 project into the plane of the cross-pieces 56 of the staples. The downwardly projecting flanges 72 of the pusher are each spaced outwardly of the belt 40 and are adapted to associate with the cross-pieces 56 of the forwardmost staple 50a as the staple is being advanced. The rear surfaces 73 of the downwardly projecting flanges 72 are sloped to allow the front of the pusher 70 to be moved out of the plane of the belt 40 and staples 50 during its return stroke.

As shown in FIG. 8, the forward end of the pusher 70 has a longitudinally extending cut out portion 74 which defines inwardly sloping sections 76, sidewalls 77 and a base 78 adapted to cooperate with the staples 50 during the staple forming operation. A further cut out portion 79 extends longitudinally rearward from the base 78 of the cut out portion 74 to accommodate a portion of a spring mechanism which will be discussed below.

Referring to FIGS. 8 and 12-15, the pusher 70 is provided with means for advancing the belt 40 and the staples 50 mounted thereon. This means comprises a spring pawl 80 which is positioned, when tensioned, in a longitudinally extending opening 82 in the pusher. The spring pawl 80 has a stepped configuration. The first step 84 is adapted to be acted upon to cam the spring pawl 80 into the plane of the staples 50 during the forward stroke of pusher 70. The second step 86 is to allow the end 88 of the spring pawl to abut against one of the staples 50 in such a manner that the spring pawl does not interfere with the remainder of the staples 50. When tensioned, the end 88 of the spring pawl extends into the longitudinally extending groove 46 in the belt and is adapted to abut against the rear surface of the transverse center section 58 of one of the staples 50.

The end 88 of the spring pawl is longitudinally spaced from the downwardly projecting flanges 72 of the pusher 70 a distance such that when cammed down it will engage the second staple 50b in the cartridge and move the belt 40 and staples 50 carried thereon forward one "staple pitch" as the pusher 70 is forming a staple. A "staple pitch" is defined as that distance which is required to move the second staple from its readiness position into a position ready to be formed around the anvil. Thus, in FIG. 7, one staple pitch is shown at "A". Finally, as shown in FIGS. 2 and 5, the pusher 70 includes a longitudinally extending opening 90 positioned at its rear end which is adapted to associate with a thrust bar 92 or the like of the surgical stapling instrument 12.

Figure 2:
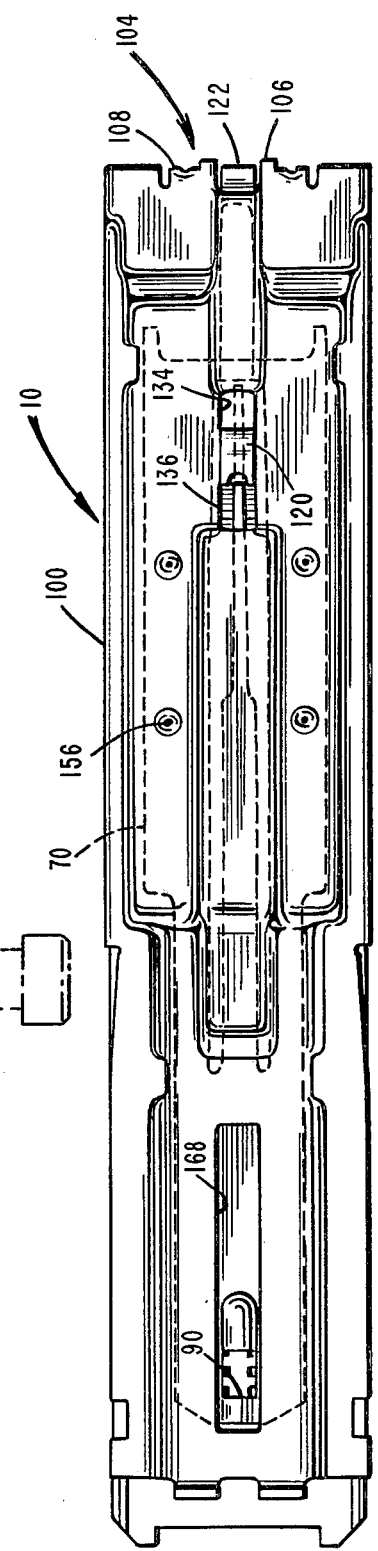
FIG. 2 is a top plan view of the cartridge taken along line 2—2 in FIG. 1.
Figure 3:
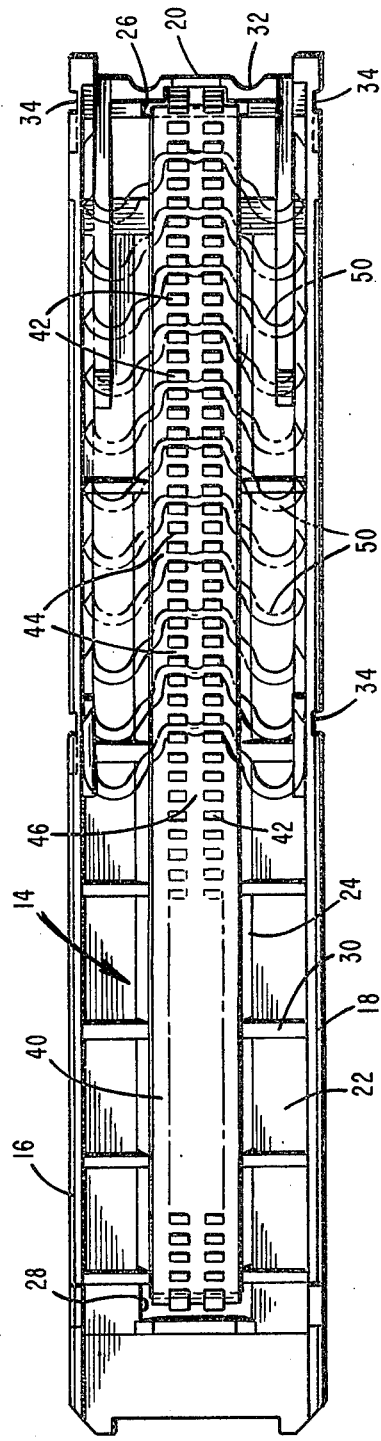
FIG. 3 is a top plan view of the cartridge with the cover removed.

With reference to FIGS. 1, 2 and 4, a cover 100, typically made of metal, encloses the main body 14 of the cartridge at the top thereof and, with reference to FIGS. 9 and 10 a plate 102 encloses the main body 14 at its bottom. The cover 100 defines an anvil 104 which includes two transversely spaced apart sections 106 and 108 at the forward end thereof. The anvil sections 106, 108 are spaced apart a distance such that the inner surfaces of the anvil sections are adapted to be abutted against by the transverse center sections 58 of the staples and to locate and center the staples prior to and while the staples are being bent into their final configuration. The anvil sections 106, 108 have a stepped configuration which cooperates with the staples 50 and the pusher 70 to form the staples into the desired final configuration.

As shown in FIG. 12, an ejection and pawl spring 120 is attached to the forward end of the cover 100. This spring 120 extends longitudinally of the cartridge 10 and, at the forward end of the cartridge, has a portion positioned intermediate the pusher 70 and the cover 100. The tip 122 of the spring 120 comprises a spring ejector which serves to eject the staples 50 once they are formed around the anvil 104. A downwardly projecting section 124 of the spring 120 is formed adjacent the tip 122 of the spring. This projection 124 is adapted, as will be described in more detail below, to fit behind the transverse center section 58 of a staple 50 once it is abutted against the anvil 104 to firmly hold the staple in position while it is being formed around the anvil.

The rear end of the spring 120 is formed into a pair of spring pawls 130 and 132, with pawl 130 being of shorter length than pawl 132. As shown in FIG. 2, the portion of spring 120 intermediate the tip 122 and the pawls 130, 132 extends through openings 134 and 136 in the cover 100 in order to securely mount the spring to the cover. The purpose of the spring pawls 130, 132 is to prevent the movement of the belt 40 and the staples 50 carried thereon in a direction away from the anvil 104 when the pusher 70 is making its return stroke. More specifically, the pair of spring pawls 130, 132 extend, when relaxed, through opening 82 in pusher 70 into the plane of the teeth 42. In this position, the ends 138 and 140 of the spring pawls 130 and 132, respectively, abut against teeth 42 and prevent the belt 40 from moving in the rearward direction relative to the cartridge 10. The spring pawls 130 and 132 are of different lengths in order to ensure good contact with the teeth 42 and to provide for tolerances in manufacturing. The spring pawls 130, 132 are flexible, however, so that when belt 40 and the staples 50 supported thereon move in the direction of the anvils 104, the pawls are cammed out of the plane of the belt teeth and staples. The spring pawls 130, 132 are spaced apart to allow for movement of spring pawl 80 therebetween.

As shown in FIGS. 1, 4 and 10 through 15, the cover 100 also includes a raised portion 150 which defines a raised surface 152 so that when the pusher 70 is in the rearward part of its stroke, the end 88 of the spring pawl 80 is above the staples 50. The cover 100 also includes a portion 151 which defines an edge 153 which acts on step 84 of spring pawl 80 to cam the spring pawl into the plane of staples 50 at the forward end of the pusher's stroke. A further raised portion 154 of cover 100 provides a space 155 for the forward end of pusher 70 to move upward and for flanges 72 to be cammed out of the plane of staples 50 on its return stroke. The intermediate section 71 of the pusher 70 flexes to accomplish this camming action. Projections 156 on the bottom surface of cover 100 provide a guide for the pusher 70 and ensure that it remains properly positioned.

The cover 100 is attached to the body 14 of the cartridge 10 by means of spring projections 160 which extend inwardly from the side portions 162 and 164 of the cover. These projections 160 fit into the slots 34 formed in the side walls 16 and 18 of the main body 14 of the cartridge. In this manner, the cover 100 may be placed over the main body 14, pushed downward, and then moved rearward to lock the cover in place. Finally, the cover 100 defines a pair of tabs 166 for mounting the cartridge 10 on the surgical stapling instrument 12 and a slot 168 for associating with thrust bar 92.

With reference now to FIGS. 8a and 9, the staple guiding mechanism of the cartridge 10 will be described. Over a front portion of the length of the cartridge body 14, the cross-pieces 56 of the staples 50 are guided along ledges 170 spaced from the respective side walls 16 and 18 of the main body 14. Near the front face 20 of the cartridge, the staples 50 are acted upon by two sets of ramps 172 and 174, respectively. The ramps 172 are spaced apart so as to act on the arms 52 of the staples, while the ramps 174 are spaced apart so as to act on the cross-pieces 56 of the staples. The sets of ramps 172 and 174 are longitudinally spaced apart so that when staple 50a is advanced in the direction of anvil 104, it first engages the set of ramps 172 and then the set of ramps 174 so that the arms 52 of the staples are moved out from underneath the next succeeding staple before the staples are moved into the plane of the main portion of the pusher 70.

The operation of the cartridge 10 will now be described. As seen best in FIGS. 2 and 5, the drive element or thrust bar 92 of the surgical stapling instrument 12 extends through the slot 168 of cover 100 and into the slot 90 in the rear of the pusher 70. In this position, the rear of the cartridge cover 100 associates with a corresponding notch (not shown) in the body of the instrument 12 by means of tabs 166. As will be explained below, each actuation of the instrument 12 advances the thrust bar 92 toward the anvil 104 of the cartridge 10. As in each of the commonly assigned patents described above, the movement of the pusher 70 is positively controlled by the thrust bar 92 of the surgical stapling instrument.

When the instrument 12 is actuated, the thrust bar 92 and pusher 70 move forward relative to the cartridge 10 in the direction of arrow 180. When the pusher 70 moves toward the anvil 104 of the cover 100, the downwardly extending flanges 72 contact the cross-piece 56 of the forwardmost staple 50a and move the staple forward.

Continued forward movement of the pusher 70, in the direction of arrow 180, moves the arms 52 of the forwardmost staple 50a up the set of ramps 172 and then brings the cross-piece 58 of the staple 50a into engagement with the set of ramps 174. Then, with still further movement of the pusher 70, the forwardmost staple 50a moves in the direction of arrow 184 in FIG. 9 up the sets of ramps 172 and 174, and shifts the staple from the plane of the belt 40 into the main plane of the pusher 70. As the staple 50a rises from the plane of the belt 40 into the main plane of the pusher 70, the cross-piece 56 of the staple slides along the respective forward faces of the downwardly extending flanges 72. Further movement of the pusher 70 in the direction of arrow 180 results in the transverse center section 58 of the staple abutting against the anvil sections 106 and 108 which locate and center the staple. At this point, the projection 124 on spring 120 moves into the position illustrated in FIGS. 6, 13 and 16, and holds the staple 50a against the anvil while forming of the staple commences as shown in FIG. 16.

As the forwardmost staple 50a is being formed around anvil 104, the end 88 of spring pawl 80 engages the transverse center section 58 of staple 50b as shown in FIGS. 14 and 16. Continued movement of pusher 70 causes belt 40 to move in the direction of arrow 180. Therefore, each of the staples 50 is advanced in the body of the cartridge 10. When the pusher 70 is at the forwardmost portion of its stroke, each of the staples 50 has been advanced in the body of the cartridge 10 one "staple pitch" and staple 50b is advanced into the ready position initially occupied by staple 50a.

After the staple has been formed around the anvil 104, as shown in FIG. 6 and as will be described in more detail below, the thrust bar 92 reverses its direction of travel causing the pusher 70 to begin its return stroke. The pusher 70 moves unimpeded until the sloping surfaces 73 of the downwardly projecting flanges 72 come into contact with the forwardmost staple 50 then remaining in the body of the cartridge 10. As the pusher 70 moves further rearward in the direction opposite to arrow 180, the downwardly projecting flanges 72 are cammed, by the forwardmost staple 50, out of the plane of the staples 50 in the direction of arrow 186 and ride over the staple. Also, the end 88 of spring pawl 80 moves in groove 46 of belt 40 and, in like manner to the flanges 72 of pusher 70, is cammed out of the plane of staples 50. Ultimately, the pusher 70 and spring pawl 80 take a position with the flanges 72 of pusher 70 lying behind and in the plane of the forwardmost staple 50a and the end 88 of the spring pawl lying above the cross-pieces 56 of the staples 50. This is precisely the position illustrated in FIG. 7, and hence the cartridge 10 is ready for the next firing operation.

During the return movement of the pusher 70, in the direction opposite to arrow 180, and when the sloping surfaces 73 of the flanges 72 are in contact with the cross-pieces 56 of the forwardmost staple 50a, forces are generated which tend to move the belt 40 and the staples 50 away from the anvil 104. In order to prevent this movement, spring pawls 130 and 132 are positioned to abut the teeth 42 on the belt 40. In addition, the pair of spring pawls 33 abut the arcuate sections 60 of the forwardmost staple 50a and prevent the forwardmost staple from backing up. In this manner, the forces exerted on the belt 40 when the pusher 70 is cammed over the forwardmost staple 50a do not result in actual reverse movement of the belt 40 and staples 50. However, the spring pawls 33, 130 and 132 are so designed that they do not prevent the forward movement of the belt 40 and staples 50. More specifically, when the pusher 70 drives the belt 40 to advance the staples 50, the staples cam the spring pawls 33, 130 and 132 out of the plane of the belt teeth 42 and staples 50.

With reference now to FIGS. 6, 8, and 9, the bending of the staples 50 about the anvil 104 and the ejection of the staples from the cartridge will briefly be described. The staple 50a, when in the position illustrated in solid lines in FIG. 8, has just abutted against the anvil sections 106 and 108. Movement of the pusher 70 in the direction of arrow 180 from this position causes the staple 50a to be bent as shown in FIG. 16 in the direction of arrows 188. This bending occurs as a result of forces exerted on the staple 50a by the pusher 70 and the stepped region of the anvil sections 106 and 108. Still further movement of the pusher 70 causes the staple to take the shape illustrated in solid lines in FIG. 6, the final bending of the staple being the result of forces generated by the pusher 70, particularly the base 78 and side walls 77 of the cutout section 74, and the anvil sections 106 and 108.

Referring to FIGS. 6 and 8, in the formation of the staple, the points 54 of the staple arms 52 enclose a large amount of fascia 191 as the arms 54 sweep through an arc illustrated by arrows 188 during staple formation. Also, after formation, the points 54 of the staple abut against the transverse center section 58 of the staple to form a staple configuration which well resists tension forces of the fascia in the direction of arrow 192. Also, staple 50, shown here made of wire of round cross-section, has flat 59 formed in the center of transverse center section 58. This flat provides a surface for points 54 to strike at the final stage of staple formation to prevent the points 54 from skewing to either side of the wire as could occur if this section of the staple were round. After being formed, the staple 50 comprises two generally arcuate sections 195 having centers 197. In this final configuration, the transverse center section 58 lies near a line drawn between the centers 197 of the arcuate sections 195. This geometry gives the staple high strength to resist the tension forces 192 of the fascia by reducing the bending moment in transverse center section 58.

After the staple is completely formed as shown in FIG. 6, and the pusher 70 begins its return stroke, the staple is ejected from the cartridge. This is accomplished by the tip 122 of spring 120 which moves downward forcing the formed staple to slide down the rear surface of the anvil 104 and be ejected from the cartridge as shown in FIG. 12. The arcuate section of the staple has a similar shape, after formation, as the pair of concave recesses 32 in the front wall 20 of the cartridge, thereby allowing the formed staple to be ejected.

Above there has been described a specific embodiment of the present invention. It should be noted, however, that the above description was given for illustrative purposes only and that many alterations and modifications may be practiced by those skilled in the art without departing from the spirit or the scope of the present invention. It is the intent therefore that the present invention not be limited to the above but be limited only as defined in the appended claims.

What is claimed is:

1. A staple-carrying cartridge comprising: an elongate main body for associating with a stapling instrument having a forward end for the formation of staples in living tissue; a belt mounted for movement longitudinally relative to said main body and adapted to carry a plurality of surgical staples; a pusher mounted in said main body for longitudinal movement relative to said main body, said pusher having at least one downwardly projecting driving surface integral with said pusher adapted to extend into the plane of said staples; ramp means for singly moving said staples out of said belt and into the plane of said pusher, said at least one driving surface being adapted to move the forwardmost staple in said cartridge up said ramp means and into the plane of said pusher; spring pawl means associated with said pusher for advancing said belt and said staples in said cartridge; and anvil means associated with the forward end of said main body.

2. The cartridge of claim 1 and further comprising a pair of spring pawls which extend into the plane of said belt and prevent the movement of said belt and the staples carried thereon away from said anvil means when said pusher is making its return stroke.

3. The cartridge of claim 2 in which said pair of spring pawls is flexible so that said belt and said staples carried thereon may move in the direction of said anvil means while camming said pawls out of the plane of said belt and said staples.

4. The cartridge of claim 1 and further comprising a pair of spring pawls which extend into the plane of the forwardmost staple and prevent the movement of said forwardmost staple away from said anvil means when said pusher is making its return stroke.

5. The cartridge of claim 4 in which said pair of spring pawls is flexible so that said forwardmost staple may move in the direction of said anvil means while camming said pawls out of the plane of said forwardmost staple.

6. The cartridge of claim 1 in which said belt has a plurality of longitudinally spaced apart pairs of teeth on one side thereof between which teeth are defined a plurality of staple-carrying grooves.

7. The cartridge of claim 6 in which said staple-carrying grooves are adapted to receive transverse center sections of staples having a pair of arms terminating in points which extend in the longitudinal direction of said main body and crosspieces which include the transverse center sections which extend transversely of said arms and said belt.

8. The cartridge of claim 7 in which said staples adapted to be carried by said belt further comprise two arcuate sections connecting said arms and said transverse center sections such that said points of said staples are widely spaced apart and said transverse center sections are positioned relatively near a line drawn between said points.

9. The cartridge of claim 8 in which said at least one driving surface of said pusher comprises a pair of downwardly projecting flanges at the forward end of said pusher which project into the plane of said staples, said downwardly projecting flanges of said pusher each being spaced outwardly of said belt and being adapted to associate with the cross-piece of the forwardmost staple carried by said belt.

10. The cartridge of claim 9 in which said downwardly projecting flanges have sloped rear surfaces to allow the forward end of said pusher to be cammed out of the plane of said forwardmost staple during its return stroke.

11. The cartridge of claim 8 in which the forward end of said pusher has a longitudinally extending cut out portion which defines an inwardly sloping section, sidewalls and a base adapted to cooperate with the individual staples during the staple forming operation.

12. The cartridge of claim 8 in which said staples are carried by said belt so that said points of said staples, with the exception of the forwardmost staple, rests upon the arms of the preceding staple in "shingle" fashion.

13. The cartridge of claim 12 in which said spring pawl means extends into a longitudinally extending groove in said belt and is adapted to abut against the rear surfaces of said transverse center sections of said staples, said spring pawl means being resiliently urged into abutment with said rear surfaces of the individual staples by cooperation with said main body.

14. The cartridge of claim 12 in which said anvil means comprises two anvil sections spaced apart a distance such that the inner surfaces of said anvil sections are adapted to be abutted against by said transverse center sections of the individual staples and to locate and center said staples prior to said staples being bent into their final configuration.

15. The cartridge of claim 14 and further comprising means for ejecting said staples from said anvil means after said staples are formed around said anvil means, said ejection means comprising a spring attached to the forward end of said main body and positioned between said anvil sections.

16. The cartridge of claim 15 in which said spring further comprises a downwardly projecting portion formed adjacent the tip of said spring, said portion being adapted to fit behind said transverse center sections of the individual staples once said staples are abutted against said anvil means to hold said staples in position while they are being formed around said anvil means.

17. The cartridge of claim 12 in which said ramp means comprises ramps spaced apart so as to act on said arms of said staples and said cross-pieces of said staples.

18. The cartridge of claim 17 in which said ramps are longitudinally spaced apart so that said staples first engage a set of ramps acting on said arms and then a set of ramps acting on said cross-pieces so that the forwardmost staple is moved out from underneath the next succeeding staple before said staple is moved into the plane of said pusher.

19. A staple-carrying cartridge comprising: an elongate main body for associating with a stapling instrument having a forward end for the formation of staples in living tissue; a belt mounted for movement longitudinally relative to said main body and adapted to carry a plurality of surgical staples; a pusher mounted in said main body for longitudinal movement relative to said main body, said pusher having at least one downwardly projecting driving surface integral with said pusher adapted to extend into the plane of said staples; ramp means for singly moving said staples out of said belt and into the plane of said pusher, said at least one driving surface being adapted to move the forwardmost staple in said cartridge up said ramp means and into the plane of said pusher; means associated with said pusher for advancing said belt and said staples in said cartridge; anvil means associated with the forward end of said main body; and means for ejecting said staples from said anvil means after said staples are formed around said anvil means, said ejection means comprising a spring attached to the forward end of said main body, said spring comprising a downwardly projecting portion formed adjacent the tip of said spring, said portion being adapted to fit behind said transverse center sections of the individual staples once said staples are abutted against said anvil means to hold said staples in position while they are being formed around said anvil means.

20. A staple-carrying cartridge comprising: an elongate main body for associating with a stapling instrument having a forward end for the formation of staples in living tissue; a belt mounted for movement longitudinally relative to said main body and adapted to carry a plurality of surgical staples; a pusher mounted in said main body for longitudinal movement relative to said main body, said pusher having at least one downwardly projecting driving surface integral with said pusher adapted to extend into the plane of said staples; ramp means for singly moving said staples out of said belt and into the plane of said pusher, said at least one driving surface being adapted to move the forwardmost staple in said cartridge up said ramp means and into the plane of said pusher; spring pawl means associated with said pusher for advancing said belt and said staples in said cartridge after said first staple has been moved into the plane of said pusher; and anvil means associated with the forward end of said main body.

* * * * *